United States Patent
Worsoee

(10) Patent No.: US 8,007,483 B2
(45) Date of Patent: *Aug. 30, 2011

(54) OSTOMY BAG FILTER WITH INTERACTIVE SURFACES

(75) Inventor: Bjarne Worsoee, Tikoeb (DK)

(73) Assignee: Coloplast A/S, Humlebaek (DK)

( * ) Notice: Subject to any disclaimer, the term of this patent is extended or adjusted under 35 U.S.C. 154(b) by 801 days.

This patent is subject to a terminal disclaimer.

(21) Appl. No.: 11/922,757

(22) PCT Filed: Jun. 28, 2006

(86) PCT No.: PCT/DK2006/000383
§ 371 (c)(1),
(2), (4) Date: Dec. 21, 2007

(87) PCT Pub. No.: WO2007/000168
PCT Pub. Date: Jan. 4, 2007

(65) Prior Publication Data
US 2009/0227973 A1    Sep. 10, 2009

(30) Foreign Application Priority Data
Jun. 28, 2005    (DK) ............................... 2005 00962

(51) Int. Cl.
*A61F 5/44* (2006.01)
(52) U.S. Cl. ........ 604/333; 604/331; 604/332; 604/334; 604/335; 604/336; 604/337; 604/338; 604/339; 604/341; 604/359; 604/360
(58) Field of Classification Search .................. 604/333, 604/337, 331, 332, 334–336, 339, 341, 360, 604/359
See application file for complete search history.

(56) References Cited

U.S. PATENT DOCUMENTS

| | | | |
|---|---|---|---|
| 3,324,856 A | | 6/1967 | Young |
| 4,387,712 A | | 6/1983 | Briggs et al. |
| 4,411,659 A | | 10/1983 | Jensen et al. |
| 4,479,818 A | | 10/1984 | Briggs et al. |
| 4,779,346 A | | 10/1988 | Schafer |
| 5,306,264 A | * | 4/1994 | Ferguson et al. ............. 604/333 |
| 5,606,748 A | | 3/1997 | Fujiwara |
| 5,643,234 A | * | 7/1997 | Lesko ........................... 604/333 |
| 5,672,163 A | | 9/1997 | Ferreira et al. |
| 5,690,622 A | * | 11/1997 | Smith et al. ................... 604/333 |
| 5,733,271 A | * | 3/1998 | Bjørn ............................ 604/333 |

(Continued)

FOREIGN PATENT DOCUMENTS
DE    3401 353    7/1985
(Continued)

*Primary Examiner* — Melanie J Hand
*Assistant Examiner* — Ginger T Chapman
(74) *Attorney, Agent, or Firm* — Coloplast Corp., Coloplast A/S; Daniel G. Chapik; Nicholas R. Baumann

(57) ABSTRACT

An ostomy bag with a filter assembly having a gas filter and a pre-filter for preventing or delaying solid/semisolid matter and liquid from reaching the gas filter. The pre-filter is at least substantially flat and comprises a number of constrictions, such as ribs extending along and between two inner surface parts of the channel. These constrictions/ribs form narrower and wider passages where the gas may more quickly pass a narrow passage and where the wider passages tend to receive and hold the liquid, solid matter and semisolid matter. At least a part of one of the surfaces may comprise an interactive agent adapted to interact with the fluid passing through the gas channel.

9 Claims, 5 Drawing Sheets

U.S. PATENT DOCUMENTS

Figure 1:
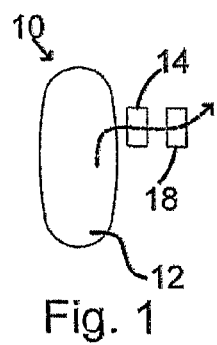

| | | | |
|---|---|---|---|
| 5,749,149 A | 5/1998 | Claytor | |
| 6,129,716 A * | 10/2000 | Steer | 604/333 |
| 6,135,986 A * | 10/2000 | Leisner et al. | 604/322 |
| 6,202,222 B1 | 3/2001 | Robbins | |
| 6,276,175 B1 | 8/2001 | Browder, Jr. | |
| 7,435,380 B2 * | 10/2008 | Winston | 422/27 |
| 7,789,866 B2 * | 9/2010 | Poulsen et al. | 604/333 |
| 2003/0014023 A1 | 1/2003 | Kanbara | |

FOREIGN PATENT DOCUMENTS

| | | |
|---|---|---|
| DE | 3439373 | 5/1986 |
| DE | 3608933 | 10/1987 |
| DE | 200 15 482 | 11/2000 |
| DE | 100 51 080 | 3/2002 |
| EP | 0116363 | 2/1984 |
| EP | 0 324 561 | 7/1989 |
| EP | 0475608 | 3/1992 |
| EP | 0607028 | 7/1994 |
| GB | 2 366 248 | 3/2002 |
| JP | 1310719 | 12/1989 |
| JP | 6181974 | 7/1994 |
| JP | 685024 | 12/1994 |
| WO | WO 00/25709 | 5/2000 |
| WO | WO 00/65940 | 11/2000 |
| WO | WO 00/67683 | 11/2000 |
| WO | 0134072 | 5/2001 |
| WO | 03020118 | 3/2003 |
| WO | WO 03/020188 A1 * | 3/2003 |
| WO | WO 2005/063146 A2 * | 7/2005 |

\* cited by examiner

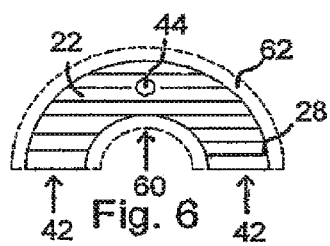
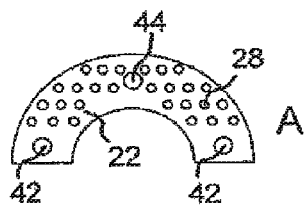
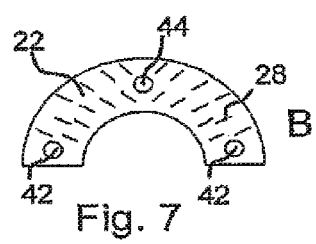
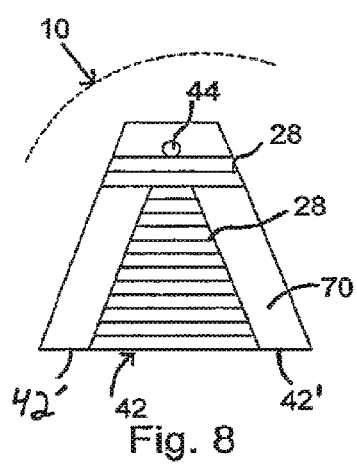
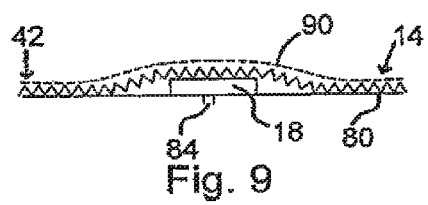
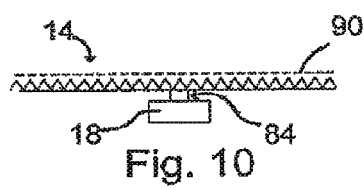
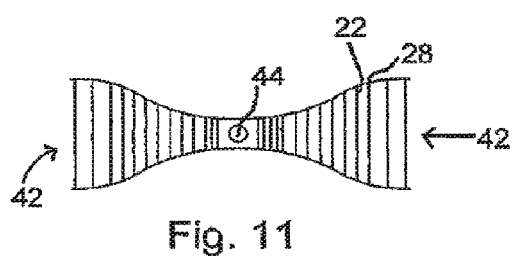
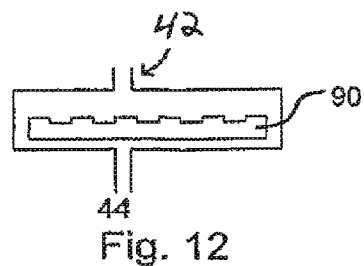

OSTOMY BAG FILTER WITH INTERACTIVE SURFACES

This is a national stage of International Application No. PCT/DK2006/000383 filed on Jun. 28, 2006 and published in English.

The present invention relates to an ostomy receiving bag having a gas filtering assembly comprising a gas filter and a pre-filter defining a plurality of restrictions between two opposed substantially liquid impermeable surfaces.

The normally used gas filter is a filter with a surface of activated carbon. This filter is sensitive to liquids and should preferably be kept dry. This can be done by means of a pre-filter.

Pre-filters of open cell foams are known in the art. Such pre-filters define multiple meandering gas paths from the ostomy bag to the gas filter. The foams, however, are not easily standardized, and the individual gas paths will comprise narrow parts which are easily clogged. One example of such a filter is known from EP-A-0 607 028.

Another kind of pre-filter defines a plurality of restrictions between two opposed surfaces. This type of pre-filter is disclosed in the applicants own application PCT/DK2004/000919 which was not published at the time of filing the present application.

Other ostomy appliances may be seen in WO98/044880, WO03/020118, WO 01/34072, U.S. 2003/0014023, U.S. Pat. No. 4,387,712, U.S. Pat. No. 4,411,659 and EP-A-0 116 363.

It is an object of the invention to provide an ostomy receiving bag wherein at least a part of the pre-filter is adapted to interact with the fluid which passes through the pre-filter, e.g. such that the properties of the fluid is changed and/or particles are removed.

In the following the fluid, which may enter the pre-filter, may be in many different physical states. The fluid can for example be in a gas state, wherein odour and small particles are transported; a liquid state; a semisolid state or so called slurry wherein the fluid can be in the shape of a relative thick liquid with random occurrences of chunks of feces; or as solid matter, where the fluid is in the shape of relative solid parts of feces, it should be understood that even when the fluid is in the shape of solid matter there will always be some liquid mixed therein.

Thus, the invention relates in a FIRST aspect to an ostomy appliance comprising a collecting bag and a gas filtering assembly positioned in a gas path from an interior of the collecting bag to the surroundings, the gas filtering assembly comprising, in the flow direction of the gas from the interior to the surroundings, a pre-filter and a gas filter, wherein the pre-filter comprises a gas entrance,
a gas exit, and
a gas channel defined between the gas entrance and the gas exit, the gas channel having two opposed, at least substantially liquid impermeable surfaces defining there between a number of constrictions each having a predetermined, largest width, wherein the distance between the two opposed surfaces, at the constriction(s), is significantly smaller than the largest width of the constriction, wherein at least a part of one of the surfaces comprises an interactive agent adapted to interact with the fluid passing through the gas channel.

One advantage of the present invention is that the pre-filter may perform the same task as the gas-filter normally would do or it may supplement the function of the gas filter. Thus, the pre-filter may be used for deodorising the fluid passing through the gas path. Accordingly, it may be possible to reduce the size of the gas filter as the pre-filter takes part in deodorising the fluid passing the through the gas channel.

A further advantage is that the pre-filter may perform one function due to one interactive agent while the gas filter may perform another function namely deodorising the fluid passing through the filter.

The interactive agent may be provided to a part of one of the surfaces of the gas channel or to a part of both of the surfaces of the gas channel. In one embodiment one or both of the surfaces of the gas channel comprises zones that comprises different interactive agents and thus the zones perform different actions. The zones may be provided in the flow direction of the gas channel such that fluid passing through the gas channels initially is exposed to one zone having a first interactive agent, and subsequently the fluid is exposes to a second zone having a second interactive agent etc.

In one embodiment one of the opposed surfaces comprises a first interactive agent, while the opposite surface comprises a second interactive agent. Accordingly, fluid passing through the gas channel is at all times exposed to two different interactive agents.

As can be understood a large number of construction disclosing many zones of different interactive agents can be provide. For example can one type of interactive agent be arranged on one or more surfaces at the gas entrance and another interactive agent can be arranged on one or more surfaces at the gas exit. Furthermore, in the gas channel a variety of different interactive agents can be provide in separate zones or in combination within one zone.

In one embodiment the interactive agent is a deodoriser, such as an adsorber, which removes undesired smells by adsorption. Such deodoriser may be activated carbon or zeolit.

Alternatively, the interactive agent may provide hydrophilic properties to part of the gas channel. This may provide the advantage that liquid and solid matter may more easily be transported through passages/zones comprising such hydrophilic properties. As an example, it may be advantageous that the solid matter is easily transported to larger compartments inside the gas channel such that is does not block narrower passages of the gas channel.

Furthermore, the interactive agent provide hydrophobic properties to the pre-filter. Such properties may be advantageous in larger compartments of the pre-filter as solid matter and larger particles thereby will be retained in the larger compartments.

The interactive agent may also or alternatively provide oleophobic properties to the pre-filter.

In one embodiment, the interactive agent is an absorber, e.g. adapted to absorb liquid from the fluid passing through the pre-filter. Such an absorber may be made of a polyacrylate, CMC, cellulose or derivatives thereof, gums, foam or alginate or mixtures thereof. Furthermore the absorber may comprise super absorbent particles (SAP) and/or super absorbent fibres (SAF). Accordingly, the risk of contamination of the gas filter is reduced as the liquid is removed from the fluid. Furthermore, one embodiment comprises in a first zone of the pre-filter, an absorber and in a subsequent second zone a deodoriser.

The interactive agent may be a soluble material, for example a water-soluble material such as a saline crystal can be used. Accordingly, in one embodiment one of the surfaces of the pre-filter comprises particles of a water-soluble interactive agent. In the latter embodiment, the surface is initially impermeable to liquid and gas. Should one or more constrictions be choked by liquid, for example solid matter, the result is that gas cannot pass through the pre-filter. However, after a while the liquid in the matter choking the constrictions will dissolve the water-soluble interactive agent whereby new passages are defined from the surface exposed to the liquid to the opposite surface of the same substrate. These new passages may allow gas to pass through the pre-filter again.

In a SECOND aspect the invention relates to a method of making a pre-filter with an interactive surface, the pre-filter being according to the first aspect of the invention, the method comprising the steps of:

providing an pre-filter element comprising an interactive surface, and assembling the pre-filter, such that the surface comprising the interactive agent defines one of the surfaces of the pre-filter.

The pre-filter element may be made of a material comprising the interactive surface, and thus the step of providing a pre-filter may comprise the steps of providing an element having an interactive surface and cutting the element so as to provide a pre-filter element. The step of providing an element having an interactive surface may comprising the step of extruding an element having an interactive surface.

The step of providing a pre-filter may comprise the step of providing a pre-filter element comprising a surface, and adding an interactive agent to the surface.

The step of adding an interactive agent may comprise the step of spraying an interactive agent to the surface. Prior to adding the interactive agent the surface may be interactive or non-interactive.

Alternatively the interactive agent can be added to the surface by dip coating the surface. This can be done by dipping the surface into a bath wherein a solution containing the interactive agent is provided. As the surface is withdrawn from the bath the solution deposited thereon is allowed to cure and the surface can thereby be used in a pre-filter element.

Other methods for applying the interactive agent can be done by applying a solution containing the interactive agent and an adhesive. The adhesive will both bind to the interactive agent and the surface allowing.

Alternatively the interactive agent can be applied to the surface in powder form, which then is heated in order to allow the interactive agent and the surface to bind. This can for example be realised by feeding the surface and the interactive agent through a set of heated rollers. The heat and pressure from the rollers will force the interactive agent and the surface together. Such a process is in the art also known as calendering.

When calendaring the surface will typically be in the shape of a planar sheet with no constrictions. These can for example be provided by thermoforming or casting the planar sheet.

Alternatively at least a part of the surface of the pre-filter element can be injection moulded and the interactive agent can added to the surface during injection moulding. This provides for a simple and cheap method wherein the interactive agent can be added to the surface of the pre-filter element at the same time as the surface as formed.

Suitable interactive agents which can be used in the above mentioned processes and which show hydrophilic properties may include any hydrophilic natural, semi-synthetic or synthetic polymer which melt at the applied temperatures or which—at least partially dissolve in dry or pre-swollen form in the adhesive resin melts used. These preferably include gelatin, vegetable polysaccharides, such as alginates, pectins, carrageenans, or xanthan; cellulose derivatives, such as methylcellulose, hydroxypropylcellulose, hydroxyethylcellulose, hydroxypropyl methylcellulose, or sodium carboxymethylcellulose; starch and starch derivatives, galactomannan and galactomannan derivatives, polyvinyl alcohol, polyvinylpyrrolidone, vinyl-pyrrolidonevinyl-acetate-copolymers, polyethylene glycols, and polypropylene glycols.

Alternatively or additionally interactive agents having a hydrophobic properties and which can be used with the above mentioned processes could for example be polyethylene, fluoride polymer or silicone.

In a THIRD aspect the present invention relates to the use of an item having an interactive surface in a pre-filter for an ostomy appliance. Such an ostomy appliance may be any ostomy appliance such as the ostomy appliance according to the first aspect of the invention.

In a FOURTH aspect the present invention may relate to the use of an item having an interactive surface in a pre-filter. The pre-filter may be a pre-filter according to the first and/or the second aspect of the invention.

In the following the invention is described in further detail. The description relates to the first, second, third and fourth aspect of the present invention.

In the present context, the distance is "significantly smaller" if it is less than 75% of the largest width of the constriction. It should be noted that this distance preferably is determined in a direction perpendicular to a general plane of the opposed surfaces and/or it is determined to be the smallest distance between the surfaces at that point. Naturally, the distance may be less than 50%, such as less than 30%, preferably less than 20%, such as less than 10%, and it may actually be less than that, such as less than 5%, 2%, or even 1% of the width.

This distance, naturally, may vary when the ostomy bag is moved, such as during movement of the user, whereby it may be desired that the distance, in unstressed use or in an unused bag, may be zero. When a gas pressure builds up, this distance may then increase and let the gas through.

It has been found that it is the narrowing provided by the constrictions which actually performs the filtering. The constrictions will provide a channel having narrower and wider portions, where the solid/semisolid material and liquid from the ostomy bag will tend to assemble in the wider portions between the constrictions. This function is opposed to that of U.S. Pat. No. 4,411,659, where the gas travels between the grid of the ribs and the liquid/solid/semisolid matter falls between the ribs due to gravity alone.

Normally, the gas filter is adapted to filter odour from the gas, such as a filter comprising activated carbon.

When the surfaces of the gas channel are at least substantially liquid impermeable, liquid entering the gas channel will tend to remain therein (or at least exit via the gas entrance/exit). If the sides were too liquid permeable, too much liquid could enter the gas channel close to the gas exit and thereby avoid the constrictions and the filtering effect thereof.

However, the surfaces may be gas permeable so that gas may enter close to the gas exit and exit via the gas exit without reducing the efficiency or operation of the pre-filter.

Preferably, the gas channel is oblong, such as oblong in the plane of one of or both of the opposed surfaces. Preferably, the channel is oblong in the direction of the gas flow—from the entrance to the exit. Also, the gas channel may be at least substantially flat. In the present context, "substantially flat" will mean that the channel extends considerably, such as at least a factor of 1.5, such as at least 2, preferably at least a factor of 5, more in the directions of the opposed surfaces than in a direction between these surfaces. Generally, the "direction of gas flow" will be the overall direction of gas flow from entrance to exit not taking notice of the meandering paths gas may take from entrance to exit.

Preferably, a largest distance between the constriction and a neighbouring constriction is at least 1.5 times the distance between the two opposed surfaces at the constriction, such as at least 2 times the distance, preferably at least 4 times the distance between the two opposed surfaces at the constriction.

The constrictions are preferably oblong elements. The constrictions may or may not have the same cross section and size/length. The distances between pairs of the constrictions may be the same (equidistant spacing) or may differ (be periodic or not). Normally, oblong constrictions will extend in at least substantially the same direction (be at least substantially parallel), but also other types of patterns are possible. Non-oblong constrictions may e.g. be positioned in a predetermined pattern in the gas channel. It is preferred that the constrictions do not overlap in that this may provide openings through which the liquid/solid/semisolid matter may more easily flow toward the gas filter.

In one embodiment, at least one of the constrictions comprises a rib extending along one of the opposed surfaces. In this connection, a "rib" will be an oblong constriction having at least substantially the same cross-section along its length.

In one situation, the ribs extend along the direction of flow in the gas channel. In this manner, the ribs will, there between, form a plurality of gas paths along the gas channel. If one path is blocked, the gas may travel under or around one of the ribs of that path and into another path and continue toward the gas filter.

In another embodiment, the ribs extend across the direction of flow in the gas channel. In this situation, the ribs form intermittent narrower and wider passages which the gas must pass order to reach the gas filter. The wider passages will act to retain matter/liquid due to the gas more easily passing the narrower paths generated by the ribs.

An interesting aspect is one where at least one of the constrictions has a cross section having, at one side thereof, a concave part adapted to receive solid or liquid material. Preferably, this concave part is provided on a side of the constriction facing in the direction of the gas flow. In that situation, the concave part may then actually take up and/or hold the liquid/solid/semisolid matter.

In general, both the gas filter and the pre-filter may be present in the ostomy bag, they may both be positioned outside the ostomy bag, or the pre-filter may be positioned inside the ostomy bag and the gas filter may be positioned outside the ostomy bag.

In one embodiment, where both filters are present in the ostomy bag, the pre-filter may fully overlap the gas filter so that no part of the gas filter is directly exposed to the interior of the ostomy bag.

In addition, the two filters may be covered by an impermeable film being attached to the bag wall and defining entrances for the gas/liquid/solid/semisolid matter to the pre-filter. Another manner is one where the filters are covered by a non-woven material, a net, a perforated material or a micro porous membrane which allows gas to pass and which is blocked when faeces tries to enter. Thereafter, further liquid/faeces entry is possible only at the gas entrance. This again gives the desired filtering function.

Naturally, the gas channel may have any desired shape. Presently, it is preferred that the gas channel has a bent shape. This is considered the most suitable shape for use in ostomy bags. However, other shapes, such as round, oval, oblong, and an S-shape may be used. Normally, this shape is determined in the general plane of the opposed surfaces.

The constrictions may be provided only at a predetermined area of the opposed surfaces of the gas channel. In that situation, another area of the surfaces may be free from constrictions and thereby form a wide gas channel. This constriction-free part may be provided close to the gas outlet of the pre-filter and is preferably positioned at a higher position, in relation to the majority of the pre-filter constrictions in order to have liquid/solid/semisolid matter, due to gravity, tend to stay away from the gas exit and the gas filter.

Naturally, the constrictions in the gas channel may have different lengths. In one embodiment, the longer constrictions are positioned closer to the entrance than the constrictions of shorter length. In this manner, the longer constrictions forming longer channels for receiving and holding liquid/solid/semisolid matter are positioned closer to the entrance through which the liquid/solid/semisolid matter enters.

Also, the distance between constrictions may vary over the area of the opposed surfaces. In a preferred manner, the distance is larger closer to the gas entrance in order to form larger reservoirs for holding liquid/solid/semisolid matter close to the entrance where it enters the pre-filter.

The constrictions may be provided in a wide variety of manners. One manner is the providing of the constrictions by forming these in e.g. a foil forming one of the two opposed surfaces of the gas channel. This forming may be a deformation, such as one based on heating and stretching of the foil. In that manner, a very simple manufacture of the present pre-filter is obtained (such as by simply combining this deformed foil and a straight foil).

Another manner is to provide the constrictions between two foils, where the gas channel is then formed between the constrictions and one of the foils. If the constrictions are provided as individual constrictions, the gas channel will be formed by one of the opposed surfaces being one foil and the other opposed surface being formed by the constrictions and the other foil.

In another embodiment, however, the constrictions are provided as a monolithic element. Then, the gas channel is formed by, on the one side, the monolithic element, and, on the other side, a part of the appliance, such as a foil thereof. This eases the manufacture and assembly of the filter assembly and ostomy bag. The monolithic element may be prepared in any suitable manner, such as by extrusion, moulding or the like.

In one embodiment, the monolithic element further comprises means for engaging or attachment to a part of the bag so as to define the gas channel between the monolithic element and the part of the bag. In that manner, the gas channel is defined by the wall and the monolithic element of the pre-filter, which makes the manufacture and assembly quite fast. This corresponds to replacing the above deformed foil by the monolithic element. The engaging means may be parts without constrictions and which are attachable directly to the bag wall using heat welding, laser welding, HF welding, adhesives or the like.

Also, it may be desired that the monolithic element is at least substantially flat having two main sides, and has one or more constrictions on each of the two main sides. In that manner, two parallel gas channels may be formed, whereby the filtering may be performed on both sides of the element.

Figure 2:
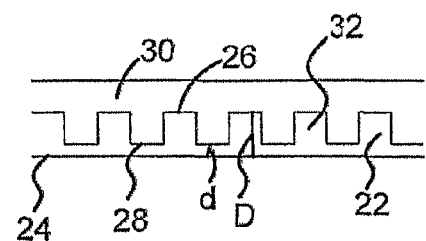
Figure 3:
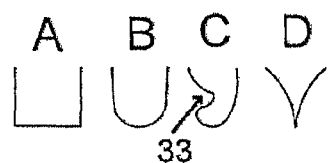
Figure 4:
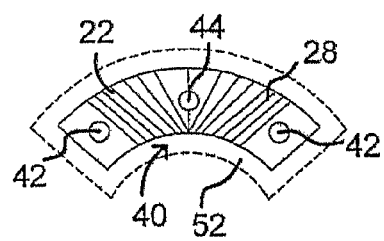
Figure 5:
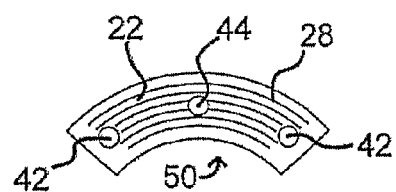

In the following, preferred embodiments of the invention will be described with reference to the drawing, wherein:

FIG. 1 illustrates a cross section of an ostomy bag with a gas filter and a pre-filter, FIG. 2 illustrates a first embodiment of the pre-filter, FIG. 3 illustrates different cross sections of constrictions, FIG. 4 illustrates, seen from above, a second preferred embodiment of a pre-filter, FIG. 5 illustrates, seen from above, a third preferred embodiment of a pre-filter, FIG. 6 illustrates, seen from above, a fourth preferred embodiment of a pre-filter, FIG. 7 illustrates, seen from above, a fifth preferred embodiment of a pre-filter, FIG. 8 illustrates an embodiment of the pre-filter wherein constriction-free areas are used, FIG. 9 illustrates a first embodiment with a first position of the gas filter and the pre-filter, FIG. 10 illustrates a second embodiment with another position of the gas filter and the pre-filter, FIG. 11 illustrates yet another embodiment of a pre-filter, FIG. 12 illustrates a last embodiment of a pre-filter, and FIGS. 13a-14b illustrate a pre-filter with an interactive surface.

In FIG. 1, the overall structure of an ostomy bag of the present type is illustrated in a cross section. It is seen that the bag 10 has a container 12, and, in the direction of flow of the gas from the container 12 to the surroundings as illustrated by the arrow, a pre-filter 14 and a gas filter 18.

The function of the gas filter 18 is to deodorize the gas received from the stoma (not illustrated). Normally, this gas filter 18 is an open cell foam comprising activated carbon for performing the actual deodorization. The gas filter may also comprise a membrane. Gas filters and membranes of this type may be seen in WO98/44880 and WO03/020188.

The function of the pre-filter 14 is to prevent or delay the liquids and solid/semisolid matter in the container 12 from reaching the filter 18.

FIG. 2 illustrates a first embodiment of the pre-filter 14 according to the invention. This pre-filter 14 comprises a gas channel 22 defined by a first surface 24 and a second surface 26 forming a number of constrictions 28. In fact, the constrictions 28 and surface 26 are preferably parts of the same ribbed, monolithic element 30. In the present embodiment, the gas channel 22 is flat and extends in the left/right direction (direction of flow of the gas as illustrated by the arrow) and the direction out of the plane of the figure.

The function of the constrictions 28 is that when gas travels in the direction of the arrow together with liquid and solid/semisolid matter, the gas will tend to force the liquid/solid/semisolid matter under the constrictions 28 toward the gas filter 18. However, due to the constrictions 28, the gas will travel more easily than the liquid/solid/semisolid matter, whereby the liquid etc. will, tend to accumulate in the spaces 32 between the constrictions 28 and be stored instead of immediately being forced under the next constriction 28.

The amount of liquid/solid/semisolid matter which may be stored in a space 32 depends, naturally, on the height, D, of the space and the distance between the two constrictions 28.

It is clear that the filter 14 may be widened in the direction out of the plane of the figure in order to increase the amount of gas filterable.

Also, it is clear that the filtering characteristics of the filter 14 may be controlled by e.g. the distance, d, between the constrictions 28 and the surface 24. When gas has to pass the pre-filter, a pressure is built up. Thus, the distance, d, between the constrictions 28 and the surface 24 may be zero (in an unused or unbiased state), so that the pressure itself forces the gas under the constrictions 28.

Also, as is clear from FIG. 3, an infinite number of different cross sections of the constrictions 28 may be used. Naturally, the shape of the constriction 28 will determine the gas filtering characteristics both when the person carrying the bag 10 is resting as well as when he/she is moving, whereby the distance, d, between (or the force exerted between) the constrictions 28 and the surface 24 changes.

An interesting cross section is illustrated in FIG. 3C, where a concave part 33 is provided. This concave part will act to collect and hold liquid/solid/semisolid matter and is preferably positioned on a side facing the gas flow direction (facing toward the gas exit).

FIG. 4 illustrates, seen from above, the overall structure of a preferred embodiment of the pre-filter and the gas flow therein.

The pre-filter 40 is bent and has a gas entrance 42 at each end and a gas exit 44 toward the entrance of the gas filter at the middle. The pre-filter 40 has a plurality of rib-shaped constrictions 28 extending across the gas flow direction between the entrances 42 and the exit 44.

In this embodiment, the gas and liquid/solid/semisolid matter must pass the ribs 28, and the liquid/solid/semisolid matter will, firstly, not be able to travel as swiftly under the ribs 28 as the gas, whereby the desired delay is desired. Secondly, the channels 22 between the ribs 28 will tend to receive and hold the liquid/solid/semisolid matter, whereby an additional delay is obtained.

In FIG. 4, a cover sheet 52 is illustrated for overlapping the pre-filter 40 and for actually defining the entrances 42. This sheet 52 prevents gas/liquid/solid/semisolid matter from shortcutting through the pre-filter 40.

Even though the sheet 52 overlays the pre-filter 40, it is preferred that the part of the pre-filter 40 with the ribs 28 is a single monolithic element. This eases the manufacture and assembly thereof.

The pre-filter 40 is preferably moulded due to it not being a standard product with this shape of the ribs 28.

FIG. 5 illustrates another preferred embodiment, where the pre-filter 50 has a number of rib-shaped constrictions 28 which are now oriented along the gas flow direction from the entrances 42 to the exit 44.

The ribs 28 form a number of gas channels 22 through which the gas may flow toward the exit 44. When liquid/solid/semisolid matter enters the pre-filter 40, it will tend to block the channels 22. Then, the gas flowing in a blocked channel 22 may travel under a rib 28 into another, possibly open, channel 22 and maintain its flow toward the exit 44.

FIG. 6 illustrates another preferred embodiment, where the rib-shaped constrictions 28 are again positioned across the gas flow direction in the beginning of the gas flow path in the pre-filter 60 but are at the final path more parallel to the gas flow.

In this embodiment, no sheet 52 is needed in that the pre-filter 60 comprises outer parts 62 where the ribs 28 are not present. These parts 62 are welded to the side of the ostomy bag in order to then define the gas channel. The entrances 42 may be provided by not welding the parts 62 all around the pre-filter 60 or by cutting part of previously provided parts 62 away at those positions prior to welding the remaining parts 62.

When the ribs 28 are parallel, this may be a standard product made as an endless, extruded ribbed band. The pre-filter 60 may be provided by simply cutting the desired shape from the band.

FIG. 7 illustrates two other manners of providing the constrictions. In FIG. 7a, the constrictions 28 are not oblong but more limited in extent. These constrictions preferably have a cross section as that of FIG. 3a in order to obtain an oblong filtering slot between the constriction 28 and the opposed surface 24. These constrictions may be randomly positioned or may be positioned (as illustrated) in a predefined pattern. FIG. 7b illustrates an embodiment using rib-shaped constrictions 28, but where the ribs 28 do not extend from one side to the other of the filter but rather extend only a part of that width. Nevertheless, a good filtering is expected from this filter.

FIG. 8 illustrates an interesting embodiment, where the rib-shaped constrictions 28 and channels 22 do not cover the full area of the gas channel. In this embodiment, two areas 70 are present in which no ribs 28 are present.

In this embodiment, the entrance 42 opens only to the part where the ribs 28 are present and is simply an open end of the pre-filter with direct access to the interior of the ostomy bag.

The areas 70 act to assemble liquid/solid/semisolid matter from the channels 22 and to, if the exit 44 is positioned higher than the entrance 42, either store this therein or to re-emit it to the bag 10 via valves 42', such as lip valves formed by two parts of foil and which act to expel liquid/solid/semisolid matter from the areas 70 and counteract entrance of liquid/solid/semisolid matter from the bag to the areas 70.

Close to the exit 44, the ribs 28 extend across the full width of the gas channel in order to prevent accidental contact between liquid/solid/semisolid matter in the areas 70 and the exit 44 due to e.g. compressing or other movement of the bag 10.

This embodiment also illustrates that it is quite possible to provide different lengths of the ribs 28 and a varying width of the gas channel. It is preferred to have longer ribs 28 at the entrance 42 in order to have longer/larger channels 22 for holding as much liquid/solid/semisolid matter as possible instead of risking early clogging or requiring transport of a large amount of liquid/solid/semisolid matter to other parts of the pre-filter. See also FIG. 11.

FIGS. 9 and 10 illustrate that the filter assembly of the pre-filter 14 and the gas filter 18 may be positioned in a number of places in relation to the ostomy bag wall 80. The choices made in this respect relate mainly to choices of manufacture and not of functionality.

In the embodiment illustrated in FIG. 9, the full assembly is positioned inside the ostomy bag 10. In this embodiment, the gas enters the entrance 42, flows in the pre-filter 14 toward the gas exit of the pre-filter 14. The gas then flows through the gas filter 18 and exits the bag through an exit hole 84 provided in the bag wall 80. The pre-filter 14 covers the gas filter 18 and is welded to the bag wall 80 with weldings as described in relation to FIG. 6.

The pre-filter 14 may be covered by a plastic foil (illustrated by numeral 90) in order to define the gas entrance 42 in order to prevent liquid/solid/semisolid matter from shortcutting the filter 14 and reaching the gas filter 18.

In the embodiment illustrated in FIG. 10, the pre-filter 14 is positioned inside the bag 10, and the gas flow exiting the pre-filter 14 exits the bag wall through a gas exit 84, enters the gas filter 18 positioned outside the bag 10.

In general, just as the length and direction of the ribs/constrictions 28 (and channels 22) are variable, so is the distance between the ribs/constrictions 28 and the wall 24 and between neighbouring ribs/constrictions. Thus, a larger distance between the constrictions and the opposing surface may be desired at least at the entrance 42 in order to, in fact, facilitate transport of liquid/solid/semisolid matter to other parts of the pre-filter (instead of simply clogging the pre-filter), and a smaller distance may be desired closer to the exit 44 or the gas filter 18 in order to prevent liquid/solid/semisolid matter from reaching the exit.

In FIG. 11, again two entrances 42 are present together with the exit 44. The rib-shaped constrictions 28 extend the full width of the gas channel, but now the ribs 28 are longer (wider channel) close to the entrances 42. In addition, the distance between the ribs 28 is larger close to the entrances 42 in order to provide larger channels 22 for assembling and holding liquid/solid/semisolid matter instead of desiring that this liquid/solid/semisolid matter travels into the pre-filter 14 in order to provide space for additional liquid/solid/semisolid matter.

In FIG. 12, another manner of using a pre-filter element 90 is illustrated wherein the gas flow is around the element from a first major side thereof to the other major side thereof. The filtering process is the same, but the overall positions of the entrance 42 and exit 44 differs from the other embodiments.

It is clear from the following, that the features of the individual embodiments (d, D, length of ribs/constrictions, cross section, positioning thereof, the shape of the gas channel, the use of an impermeable sheet/non-woven or the like, welding the pre-filter to the bag, gas filter and/or pre-filter inside or outside the bag, a membrane or not etc.) may be interchanged and used in a large number of ways without deferring from the invention.

Figure 13A:
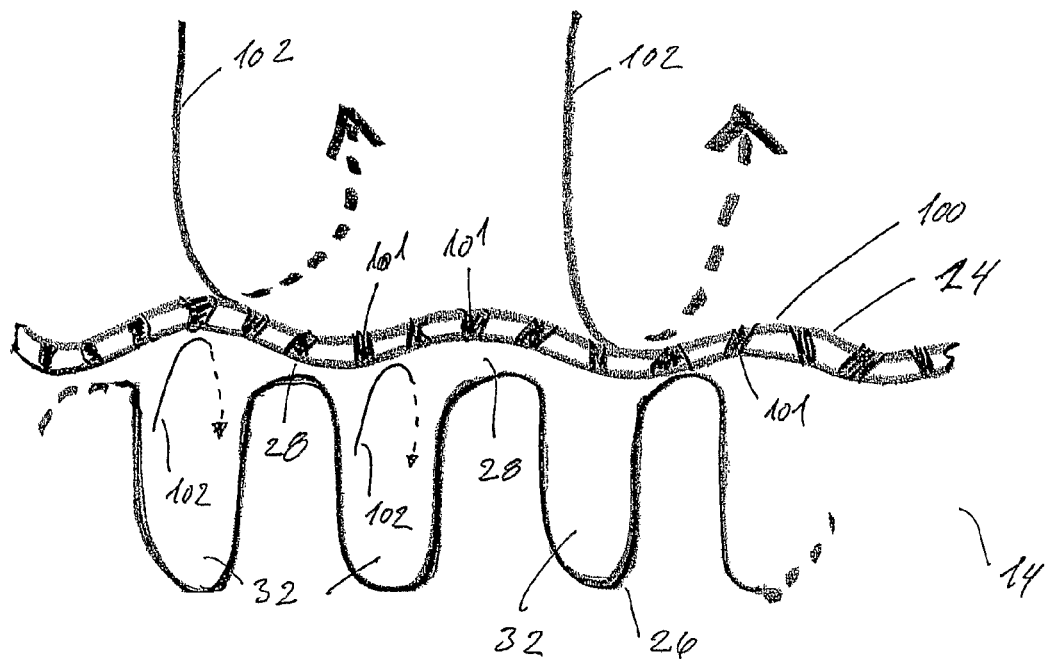
Figure 13B:
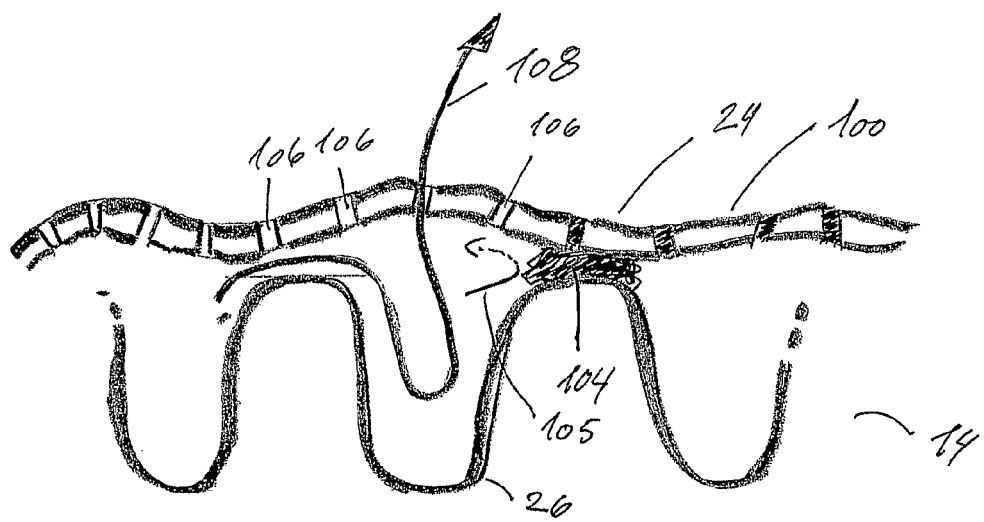
Figure 14A:
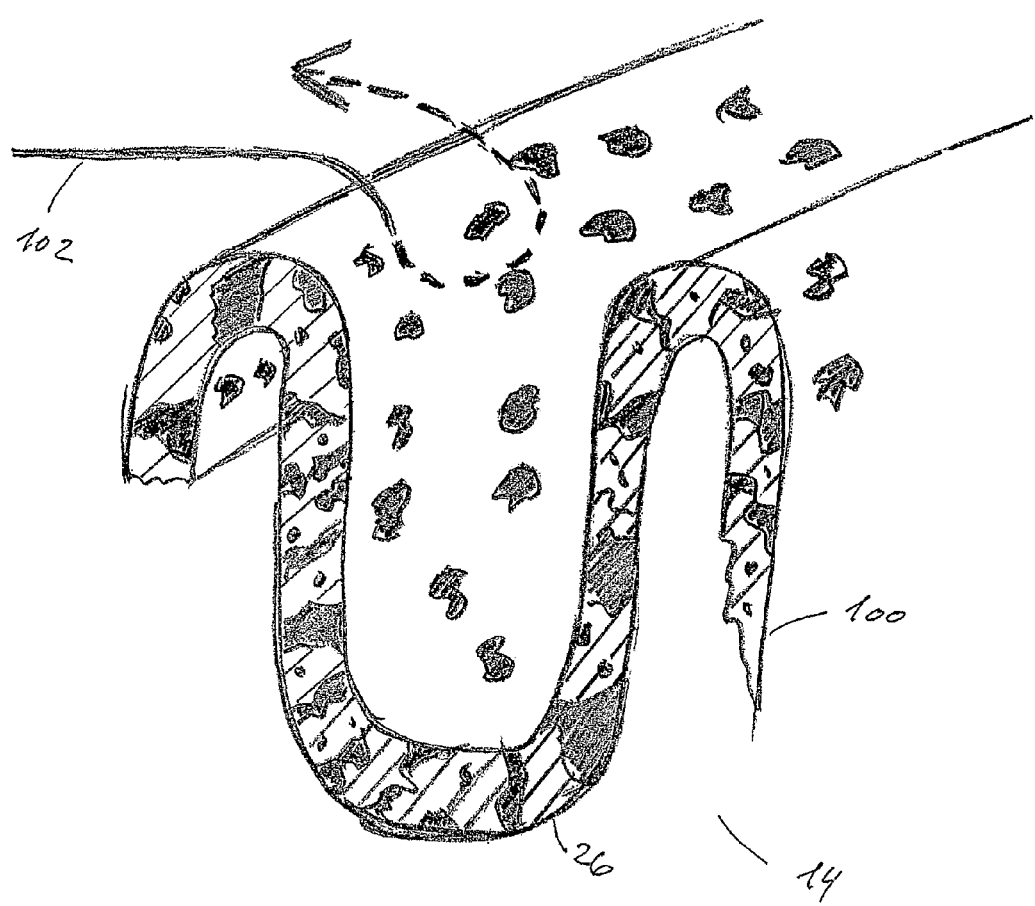
Figure 14B:
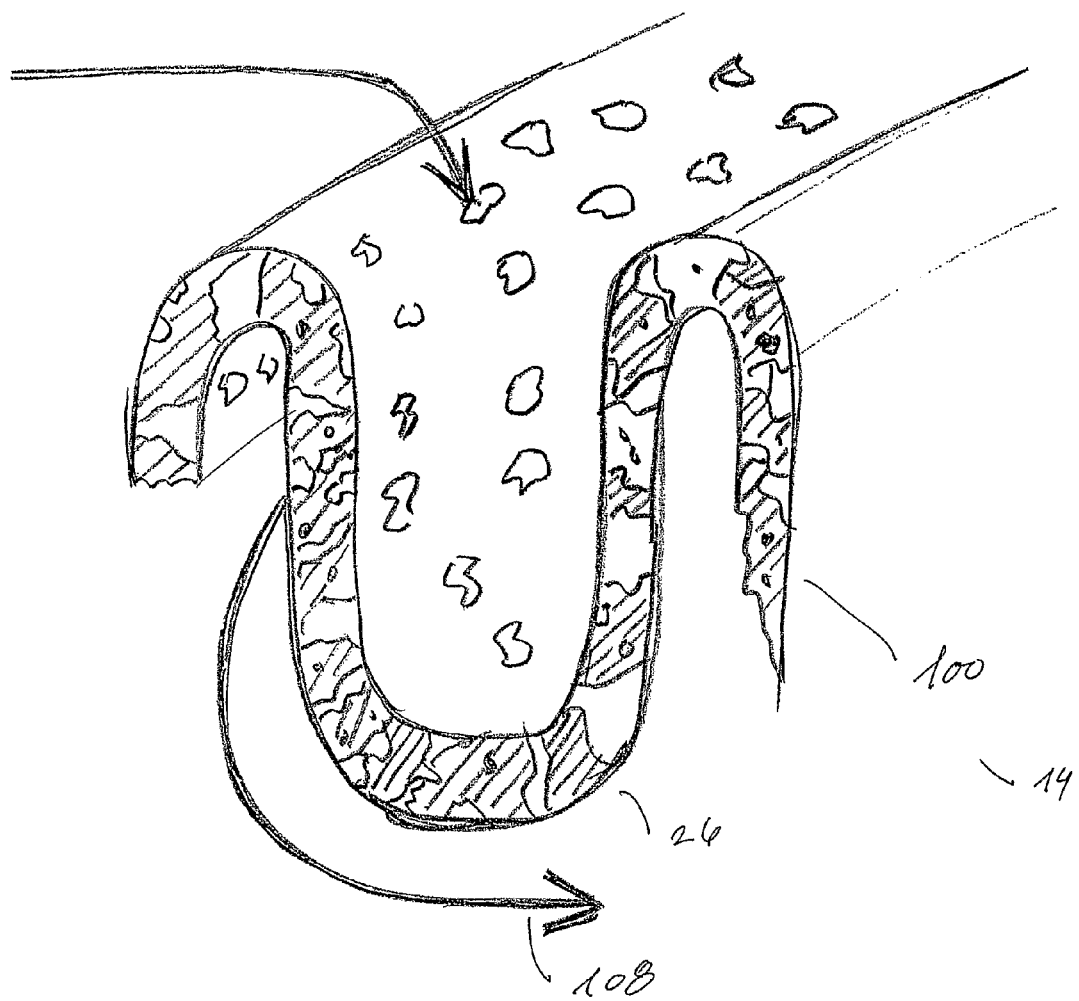

FIG. 13a-14b illustrate an interactive surface 100 of a pre-filter 14. FIGS. 13a and 13b show a substantially planar first surface 24 of the pre-filter comprising the interactive properties, while in FIG. 14a and FIG. 14b the interactive surface of the pre-filter is shown in a wave-shaped element (defining a second surface 26) such as an element defining a plurality of ribs. The interactive surface comprises a plurality of dissolvable areas 101. Said areas may be made of salt crystals. A salt has a positive metal ion and a negative counterion. Examples of metal ions could be $Na^+$, $K^+$, $Li^+$, $Ca^{2+}$ or $Mg^{2+}$. Examples of counterions could be $Cl^-$, $F^-$, $I^-$ $Br^-$, $OH^-$, or $CO_3^{2-}$ (Carbonates), $HCO_3^-$ (Bicarbonates), $PO_4^{3-}$ (Phosphates), $SO_4^{2-}$ (Sulphates), $S_2O_4^{2-}$ (sulphite), $NO_3^{2-}$ (Nitrate), or organic ions such as HCOO— (Formate), $CH_3COO^-$ (Acetate), $C_2H_5COO^-$ (Propionate), $C_2H_5OCOO^-$ (Lactate) or $C_6H_6O_7^{2-}$ (Citrat). If the areas are made by solvent casting, mono and di Saccharide or short chained polyethylenglycol may be used.

In the use situation the interactive surface initially is impermeable to liquids and solid matter as indicated by arrows 102. The pre-filter 14 is designed as described in the aforementioned and thus define a plurality of constrictions 28 and spaces 32 wherein the solid matter may accumulate. However, after a period of use one or more of the constrictions may choke as indicated by reference number 104 and thus the gas flow in the pre-filter is blocked as indicated by arrow 105. Normally, this would lead to ballooning of the ostomy bag, which consequently had to be changed. However, after a period of time the liquid of the faeces trapped upstream the clog, will dissolve the interactive zones 101 of the interactive surface and a plurality of new flow channels 106 will allow the gas to flow again as indicated by arrow 108. The result is that the ostomy appliance may be used for a longer period of time.

The invention claimed is:

1. A pre-filter for a gas filtering assembly for an ostomy appliance, the pre-filter comprising
   a gas entrance,
   a gas exit, and
   a gas channel defined between the gas entrance and the gas exit, the gas channel having two opposed, substantially liquid impermeable surfaces defining there between a number of constrictions each having a predetermined, largest width, wherein the distance between the two opposed surfaces, at the constriction(s), is significantly smaller than the largest width of the constriction, wherein at least a part of one of the substantially liquid impermeable surfaces comprises an interactive agent adapted to interact with the fluid passing through the gas channel.

2. A pre-filter according to claim 1, wherein substantially the entire surface of at least one of the surfaces comprises an interactive agent.

3. A pre-filter according to claim 1, wherein the interactive agent is a deodoriser.

4. A pre-filter according to claim 1, wherein the interactive agent provides hydrophilic properties.

5. A ore-filter according to claim 1, wherein the interactive agent provides hydrophobic properties.

6. A pre-filter according to claim 1, wherein the interactive agent is an absorber.

7. A pre-filter according to claim 1, wherein the interactive agent is soluble.

8. A pre-filter according to claim 1, wherein the interactive agent is water-soluble.

9. An ostomy appliance comprising a collecting bag and a gas filtering assembly positioned in a gas path from an interior of the collecting bag to exterior surroundings of the collecting bag, the gas filtering assembly comprising, in the flow direction of the gas from the interior to the exterior surroundings of the collecting bag, a gas filter and the pre-filter of claim 1.

* * * * *